(12) United States Patent
Kimura et al.

(10) Patent No.: US 6,276,214 B1
(45) Date of Patent: *Aug. 21, 2001

(54) STRAIN SENSOR FUNCTIONED WITH CONDUCTIVE PARTICLE-POLYMER COMPOSITES

(75) Inventors: Toyoaki Kimura, 75 Yamatogaike, Arako-cho, Nakagawa-ku, Nagoya-shi, Aichi; Tadashi Fujisaki, Tokyo, both of (JP)

(73) Assignees: Toyoaki Kimura, Aichi; Mitake Electronics Co., Ltd., Kyoto; Chubukako Corporation; MCK Corporation, both of Shizuoka, all of (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/221,065

(22) Filed: Dec. 28, 1998

(30) Foreign Application Priority Data

Dec. 26, 1997 (JP) .................................................. 9-361358

(51) Int. Cl.⁷ .................................................. G01N 3/00
(52) U.S. Cl. .................................................. 73/795
(58) Field of Search .............................. 73/760, 763, 774, 73/777, 795, 805

(56) References Cited

U.S. PATENT DOCUMENTS

| 4,208,905 | * | 6/1980 | Spoor .............................. 73/862.633 |
| 4,289,036 | * | 9/1981 | Barker .................................... 73/799 |
| 4,708,019 | * | 11/1987 | Rubner et al. ........................ 73/760 |
| 5,817,944 | * | 10/1998 | Chung .................................... 73/768 |

* cited by examiner

Primary Examiner—Max Noori
(74) Attorney, Agent, or Firm—Koda & Androlia

(57) ABSTRACT

When conductive particles are dispersed beyond the percolation threshold, electric conductive paths are formed between the electrode by chains of particles contacting with each other between the electrodes. Elongation of this composite results in an increase in the gap distances between conductive particles. This results in the increase in the electric resistance of the composites. It is found that strain sensors can be made by the use of this nature. Strains of iron frames or iron-concrete are known by the change of electric resistance of the sensors which are set on a surface of the place to be monitored. Main fields of the application of the present sensors are safety monitoring systems for buildings, bridges, tunnels, dams, etc. The sensors are also applicable for tanks of chemicals, aircraft, ships and mega-floats.

9 Claims, 15 Drawing Sheets

US 6,276,214 B1

STRAIN SENSOR FUNCTIONED WITH CONDUCTIVE PARTICLE-POLYMER COMPOSITES

BACKGROUND OF THE INVENTION

1. Field of the Invention

The present invention relates to strain sensors which function with electro-conductive particles that are hereinafter called "conductive particle-polymer composites" and in the present invention, conductive particles are dispersed in a polymer such as plastics and rubbers in order to obtain conductive polymer composites, so that electro-conductive passes formed throughout the composites are used for measuring the increase of electric resistance in the composites that is brought by the elongation of the composites caused by an external force.

The sensors of the present invention can be used, for instance, for monitoring the safety of iron frames and iron-concrete of buildings. Nowadays, buildings, bridges, framed-up roads, tunnels, dams, etc. are mainly constructed with iron frames and iron-concrete; and for countries in which earthquakes often occur, it is desirable to monitor the iron frames and iron-concrete of buildings, bridges, tunnels, and so on. With the use of the sensors of the present invention together with a computer network system, a real-time on-line monitoring of earthquakes is attainable.

The sensors of the present invention can be used not only for the constructions described above but also for monitoring the unbalanced sinking of tanks of the chemical industry by way of on-line monitoring. Furthermore, an inspection of hazardous material storing facilities such as underground tanks which are the subjects of regulations regarding the handling of hazardous material can be executed on regular working days without removing such materials from the tanks.

In addition to the example described above, the sensors of the present invention can be installed in ships, mega-floats, aircraft, and tank-trailers. Especially, a great contribution can be expected when used in the mega-floats, since the mega-floats presently need to be carried to docks for inspections; and by installing the sensors of the present invention, the number of uses of docks for inspections of the mega-floats can be reduced, which saves expenses.

2. Prior Art

Until the present, it has not been possible to inspect the damages of iron frames and iron-concrete without destroying some part thereof. Taking as an example, for the iron frames of a building, it is necessary to partly destroy the ceiling or floor and to peel off the fireproof coating from the surface of iron frames, and the damage can be seen only after these troublesome processes. Therefore, a new technique that allows an inspection of damages on iron frames and iron-concrete by using strain sensors without destroying any part of the building has been desired.

Presently, several strain sensors are known; and these are coils of resistor wire, resistors patterned on plastic films, ceramic sensors which make use of deformation of the ceramics and sensors which make use of cutting carbon fibers.

Printed sensors with a metallic powder ink looks similar to the sensor of the present invention at first sight. However, there are great differences between the two as described below.

In the case of sensors in which a conductive ink is printed, a deformation of the sensors causes a change in the resistance; and in this case, the resistance and the strain are proportional to each other. Generally, the relation between the resistance and the strain is approximately linear. Thus, a severe calibration is necessary when the sensors are installed in the building in order to determine damages caused by an earthquake. For the patterned sensors, not only the severe calibration but also a long term stability of the resistance is inevitable, because it is necessary to judge from the small variation of resistance whether the buildings are damaged or not. Since no one knows when an earthquake may occur and it may be 10 years or 100 years after the sensors are set, the stability of resistance must be effective for such a long period of time. Generally, calibration of sensors is done once per several years. It is not guaranteed that the resistance of the patterned sensors is stable over such a long period of time.

It is described above that a severe calibration is necessary for the patterned sensors. This requires that the thickness of the pattern should be constant throughout the entire sensor. This again limits the size of the sensor. Namely, it is easy to have a constant thickness for a smaller size than for a larger size. For a larger size, a great amount of severe process-control is necessary so as to obtain homogeneous properties over the entire region of the pattern. This is one of the reasons that patterned sensors of large sizes are not available.

Since printed layers of sensors consist of metal particles aggregate from ink, resistances of sensors are limited within a certain range. Volume resistances are not varied as desired. This is one of the reasons that bigger sizes are not available.

Beside the problem described above, the major disadvantage of the prior art patterned sensors is that they are small in size. Taking an example of buildings, a great deal of iron frames are used in a building. Thus, there are numerous points to be monitored. When small size sensors are used, numerous sensors are necessary to monitor a building. This results in extraordinarily high cost. This is a much harder problem for urban high ways. Therefore, the patterned sensors cannot actually be used for buildings, bridges, ships, mega-floats, urban high ways, etc.

Another disadvantage of the prior art sensors is "linear response", namely resistances increase linearly with increasing strain. Therefore, severe calibration and stability during long periods are inevitable for monitoring systems. The critical response must always be clear to determine the damages of the iron frames of buildings.

SUMARY OF THE INVENTION

The strain sensors of the present invention are formed from conductive particle-polymer composites. The stress applied on these sensors causes strain, which results in the change of electric resistance; and once the relation between strain and resistance is obtained, the strain can be obtained from the resistances of those sensors.

There are several methods to make the strain sensors of this invention. One is a molding process wherein conductive particles such as carbon are mixed with a molten polymer in a mixer such as a kneader, and the composite is made in a shape of a film. Electrodes can be obtained during or after the molding process. Another method is printing wherein a polymer is dissolved in a solvent and then conductive particles are mixed with the solution; and this solution, composed of conductive particles, the polymer and the solvent, is called ink. The sensors are made by printing on base films where electrodes have been printed already. It is also possible to make the sensors by dispersing conductive particles in the mixture of thermocured plastics and their hardening agents and then molding them.

Conductive particles in the present invention include graphite, carbon black, activated carbon, carbon fibers, carbon whiskers, fullerenes, carbon nanotubes, metallic powder, metallic foils, metallic fibers, beads and microbeads of insulators whose surfaces are changed to be conductive with carbon, and micro pieces of insulators such as mica or potassium titanate whose surfaces are also changed to be conductive by chemical plating such as CVD (chemical vapor deposition) or PVD (physical vapor deposition).

Any polymer can be used for the sensor of the present invention if the polymer has a suitable elongation limit and toughness to handle. Elongation limits necessary for the sensors depend on the application. Thus, preferable polymers are polyethylene, polypropylene, polyacrylate, polyesters, nylons, polyvinyl chloride, polyvinylidene chloride, fluoropolymers, polyvinyl acetate, polystylene, polymethylmethacrylate, polyethylmethacrylate, polyhydroxymethyl methacrylate, polyvinyl alcohol, polyacrylonitrile, polyimide, polysulfone, polycarbonate, polyacetal, polyurethane, polyphenylene oxide, polyxylene, polyformal, polybutylal, polyoxyethylene, polyoxymethylene (amorphous), copolymers of two or more monomers of which homopolymers are described above, rubbers, silicone polymers, phenol polymers, alkid polymers and cellulose polymers. Among these copolymers, the copolymer of ethylene and vinyl acetate is a useful polymer as a sensor because of its wide temperature availability and good suitabity for fitting to various constructions.

High cost sensors made of carbon fiber, coil of resistor wire and printed patterns provided on a plastic film with electro-conductive metal powder-ink are described above. Instead of these high cost sensors, the inventors have succeeded in an invention of economical sensors comprising plastics or rubbers with dispersed conductive particles. Electrical resistances of the sensors of the invention increase when elongated, and thus strains can be measured based upon the changes in the resistance. In addition to low cost, the sensors have a unique characteristic which has never been known. Namely, the output of the sensors has an exponential function of strain. This means that the output increases abruptly when the strain reaches a certain level, and it is preferable to monitor a dangerous limit of strain.

The cost of the strain sensors of the invention is definitely lower than the prior art sensors such as those of carbon fibers or patterned metallic resistors. This is because the materials of the present invention are of low a cost. Carbon black is cheaper than carbon fibers, and graphite is much cheaper. Polymers are also available at a low cost. The process to manufacture the present invention is inexpensive.

The conductive particle-polymer composites are molded or printed and then endowed with electrodes so as to form strain sensors. The sensors are installed on surfaces of structural parts such as iron frames. Lead wires are connected to the electrodes of the installed sensors. It is necessary to know the places where the sensors are installed. A long history of civil engineering and architecture provides us with enough information concerning the place to install. It is also possible to install several sensors at one place.

Monitoring systems by computers as described above make visual on-line monitoring possible, by which damaged places are recognized immediately after an earthquake. This helps a government to make efficient recovery plans; and a great contribution can be expected for a recovery of a disaster. Once there is earthquake damage to bridges, tunnels or urban highways, the visual monitoring systems promptly and exactly show the places damaged, which assists in providing a warning and a notice of quick recovery work.

The sensors of the present invention also contribute to the monitoring of unbalanced sinking of chemical tanks. On-line monitoring systems tells whether the tanks are safe or not. In some occasions, a tank continues to sink inhomogeneously but very slowly. In such a case, it does not come to a dangerous stage until a certain time. However, the system can tell when it is dangerous and needs a repair. This gives time for the schedule of repair work in advance.

As stated above, the sensors of the present invention are available for ships and mega-floats. This can shorten the interval of the inspection at a dock. From this, a considerable cut in expense can be expected.

The process of dispersing conductive particles in polymers are well developed nowadays. For example, carbon is dispersed in rubber to make tires. Another example is plane heaters. Especially, self-temperature-control heaters, which are also known as self-regulating heaters, switching heaters or PTC heaters, are now getting popular. These heaters show the following property. Electric resistance of the heaters are lower at lower temperatures but shows an abrupt jump at certain temperatures. The word switching comes from this property. At lower temperatures, the electric current flows because of lower resistance. So, this corresponds to a switch-on. When the electric current is applied, the temperature of the heater increases. When the temperature exceeds a certain level, then the current decreases abruptly because of the high resistance. This is a switch-off. The mechanism of the switching is said to be a volume expansion of matrix polymers. Some drastic changes in volume (in density of the polymer) at the switching temperature is necessary. Therefore, polymers with high crystallization is preferable.

Many researchers have recognized nowadays that the mechanism of the switching is due to the volume expansion of matrix polymers. However, some have opposed this. It is also reported that the elongation of a carbon black-polymer composite does not result in an increase in electric resistance.

Although there is some negative prospect of an increase in electric resistance when elongated, the inventors came to the conclusion that electric resistance actually increases as a result of elongation if the conductive particles and polymers are properly selected. In the case of thermal expansion, high crystalline polymers are inevitable. However, for the sensors of the present invention, crystallization of polymers is not crucial as in the case of PTC heaters. Of course, crystallization of polymers plays a role in the case of the strain sensor. This will be described later.

By starting from the mechanism of self-temperature-control heaters, the present invention of strain sensors has been successful. Polymers should be crystalline for self-temperature-control heaters except those which some of the present inventors have disclosed (Japanese Patent Application No. H9-133746). However in the case of the strain sensors of this invention, any polymer can be used as long as the polymer can be elongated by stress. Although the value of the sensor depends on the properties of the polymers used, it is important to select those depending on how they are used.

As to the conductive particles, basically any particles can be used. However, it must be selected by taking such factors into consideration as the process of manufacture and the conditions in which the sensors are used.

DETAILED DESCRIPTION OF THE INVENTION

Figure 1:
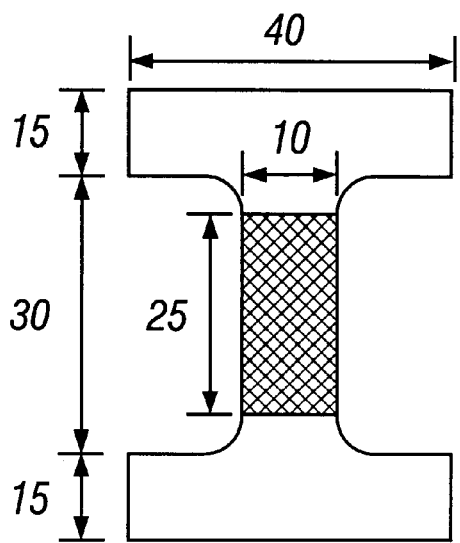
FIG. 1 is a top view indicating the form of sample sensor, the sensor being painted with a conductive silver paste except the gray part of the center (including top, bottom and side parts)

In the present invention, a desired amount of graphite was dispersed into a molten ethylene-vinyl acetate copolymer (EVA), and samples were made by a hot-press of the carbon-polymer composite. It was found that the resistance increases exponentially with the increase of the elongation of the sample.

In order to produce the strain sensors, two processes can be usually taken. One is to disperse particles in a molten polymer at a high temperature. A mixer such as a kneader is employed for this purpose, and the composite is molded after the mixing. Electrodes can be given at the time of the molding or they are fixed after molding by a procedure such as ultrasonic adhesion.

The other process is a printing method. At first, a polymer is melted into a solvent and then conductive particles are dispersed in to this polymer solution. Although any solvent can be used basically, solvents with lower boiling points are not preferred because printed layers are inhomogeneously dried at a room temperature. Therefore, a solvent such as xylene, decaline or tetraline are is actually used. On some occasions, a small amount of ethylene glycol, terpene oil, or some additive is used in order to obtain adhesibility between the printed layer and the base film.

Strain sensors can be made by the procedure described above. Resistances of strain sensors with no strain can be varied as desired. This is because resistance is a function of the concentration of conductive particles, the distance between the electrode, the length of the electrode, the thickness of the composites, type of the polymer, type of conductive particles, and so on. Therefore, sensors of a variety of size (from a few μm to a few meters) can be made by selecting the conductive particles and polymers and also by setting the electrode gap and length properly. Therefore, a variety of applications is possible for this strain sensor.

The present invention makes it possible to exponentially increase the response when the strain reaches a certain value.

In order to do so, the sensors must be designed by selecting polymers and conductive particles and setting the size after careful calculation. Such a wide selectivity has never been achieved before.

Strain sensors of the present invention are used by being set on the surface of iron frames or iron concrete. This is done by the use of an adhesive reagent, for example. When those iron frames or concrete ion frames have been strained, the sensors set on them have the same strain. This results in an exponential increase in their resistances. From the response, it is possible to judge whether those iron frames or iron concrete have been damaged or not. Critical strains in the iron frames or iron concrete are already known nowadays, and it is possible to make those sensors which give exponential increases at the critical strain.

A constant relation exists between the resistance and the strain up to an upper limit of strain. The upper limit and the change of resistance per unit strain depend on the polymer, conductive particles and also the content of particles.

Therefore, suitable sensors can be designed by taking the following two factors into full consideration: the properties of iron frames and iron enforcement in concrete and places and their sizes where those sensors are installed. In this case, designs by not only the decision of the size and shape of sensors but also the suitable selection of polymers and conductive particles for them are included.

Embodiment 1

Here, an embodiment generally describing the present invention is disclosed in detail In this embodiment a copolymer of ethylene-vinyl acetate (EVA) (manufactured by Toso, ethylene content: 80 wt %) was employed. A desired amount of EVA was dissolved in toluene to form a polymer solution. Then a calculated amount of graphite was added bit by bit in to this solution and mixed thoroughly. Then the solution was casted in a small rectangular pan with teflon coating and toluene was evaporated. The carbon-EVA composite was then dried in vacuo to take off the toluene. The composite was then hot-pressed to form a sheet (200×200×2 mm). Samples of a dumbbell shape were cut from this sheet. As shown in FIG. 1, the top, bottom and side faces of both ends were coated with a conductive silver paint (Fujikura Kasei, Dotite D-550) except for the central part (25 mm long). These painted parts were used as electrodes.

The samples were clumped at both ends covered with polyethylene films as an insulator. These samples were elongated by an apparatus, which will be described later, and the electric resistance and the elongation were measured simultaneously and, measured values were input into a computer (NEC PC-9821 V-16) through a RS-232C interface. The apparatus for the measurement of resistance and elongation was order made. Hardware was made by Kawachi Tekkou and Software by Step One. Elongation was made by a computer controlled pulse motor through several gears and a ball joint by which a smooth movement was possible. Electric resistance was measured with a digital multimeter (Advantest R6452A). Elongation was measured with a digital gauge (Sony LY41) and a sensor (DE30R). The precision of the elongation was 1 $\mu$m.

Figure 2:
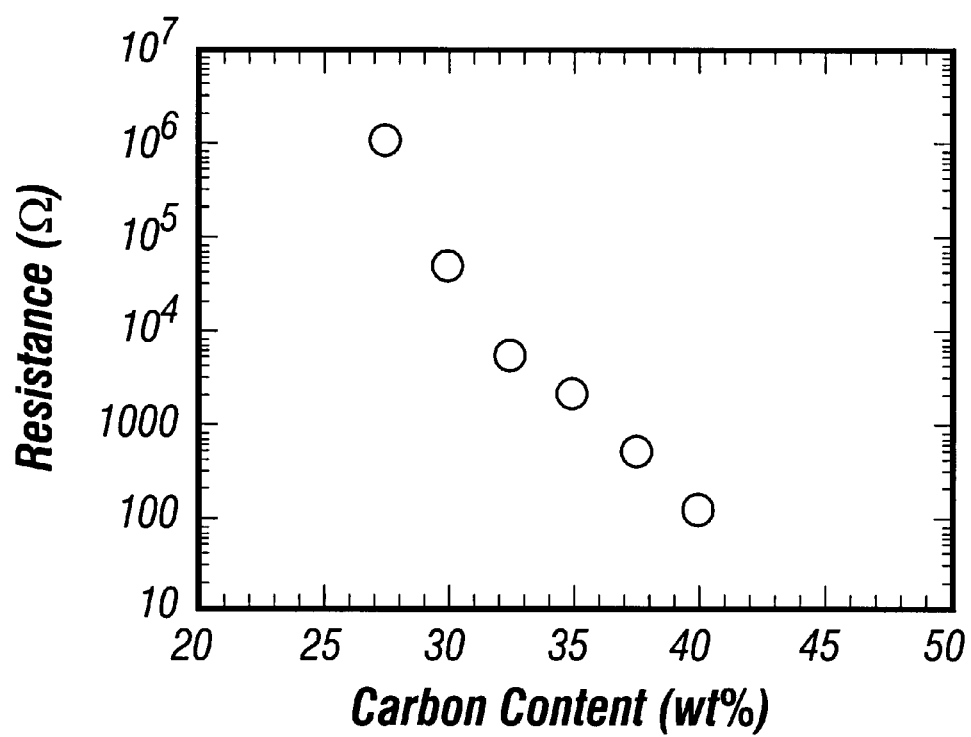
FIG. 2 is a graph indicating the relation between resistance value of the sample with no strain and the amount of carbon addition.
Figure 3:
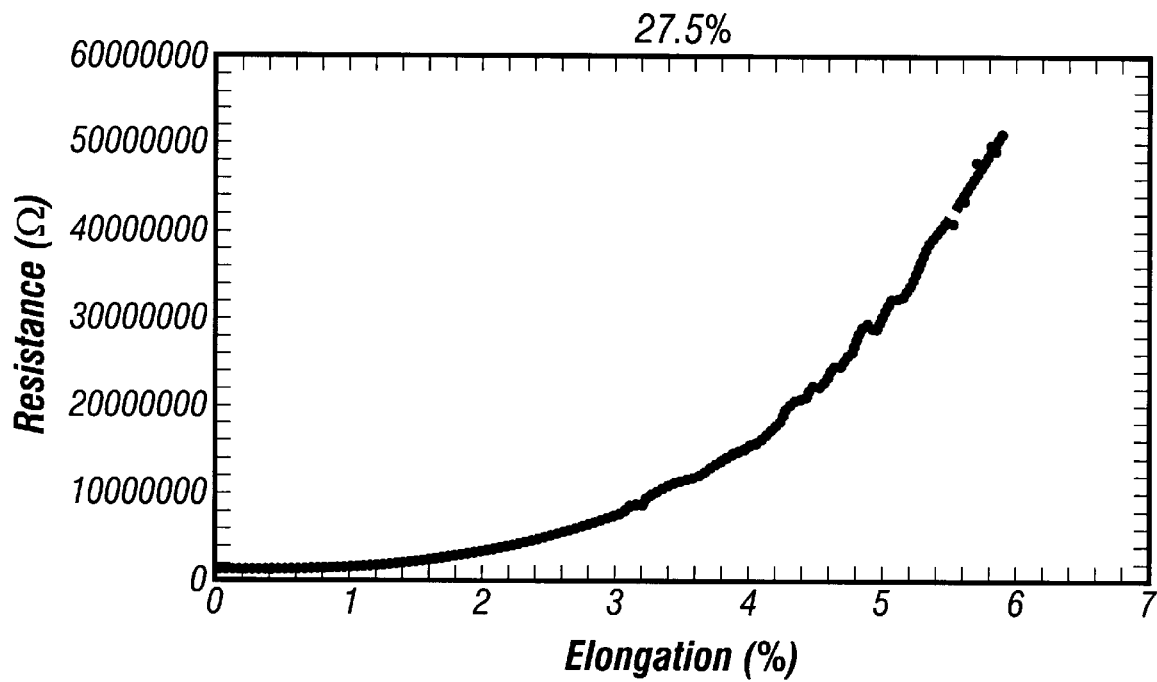
FIG. 3 is a graph indicating the relation between electric resistance of graphite-EVA (PE80 wt %) sensor and elongation (graphite concentration: 27.5 wt %)
Figure 4:
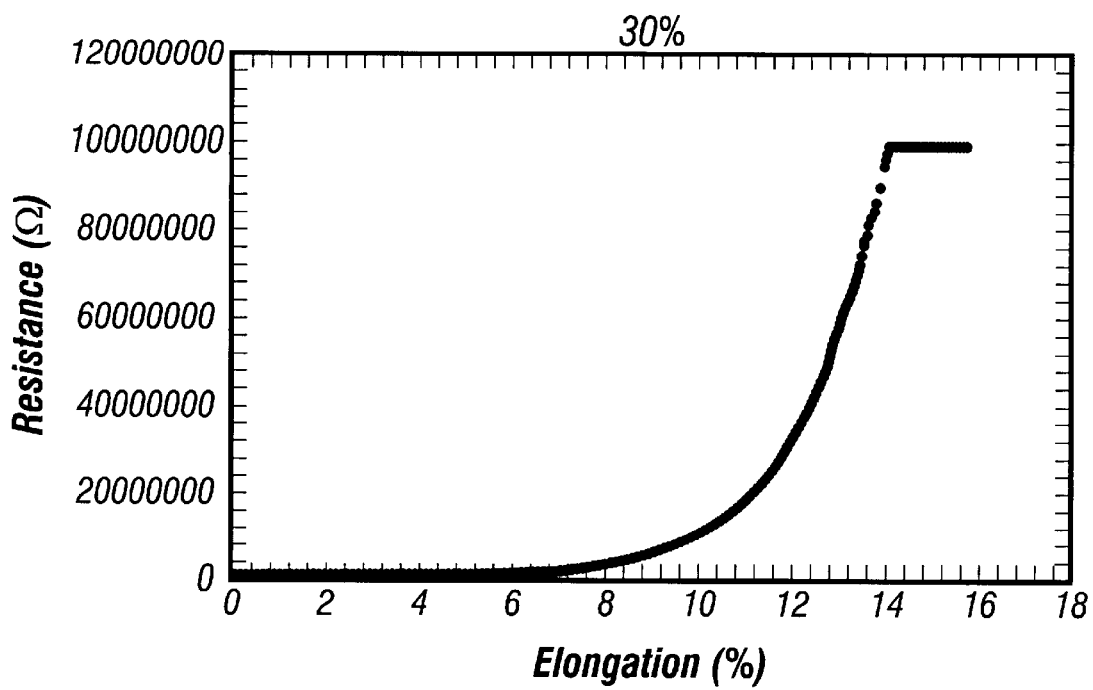
FIG. 4 is a graph indicating the relation between electric resistance of graphite-EVA (PE80 wt %) sensor and elongation (graphite concentration: 30.0 wt %)
Figure 5:
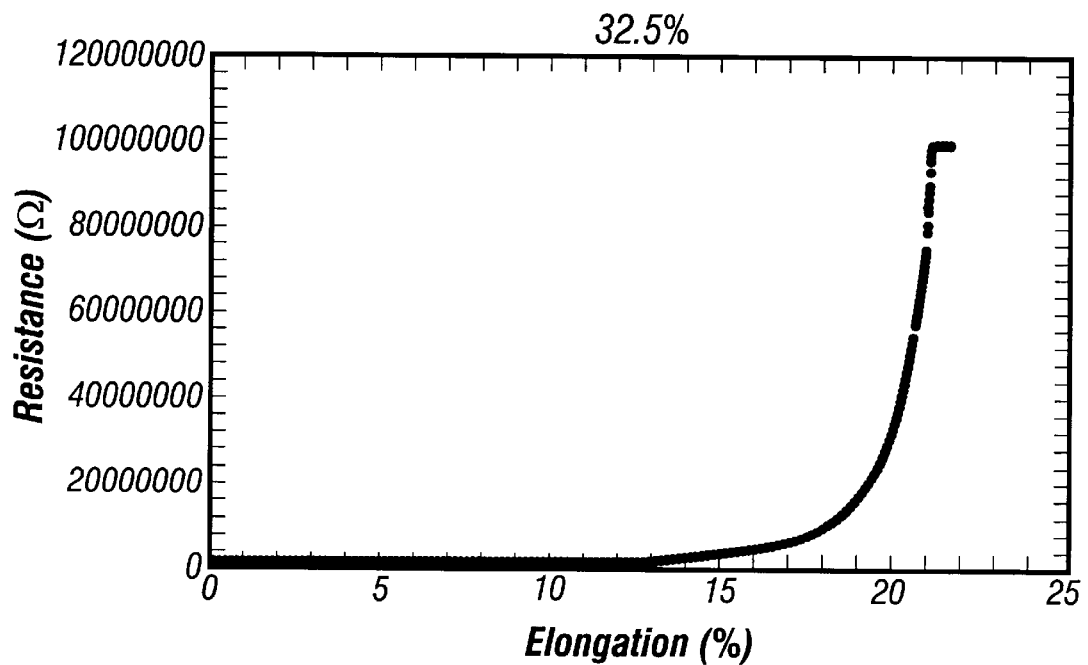
FIG. 5 is a graph indicating the relation between electric resistance of graphite-EVA (PE80 wt %) sensor and elongation (graphite concentration: 32.5 wt %)
Figure 6:
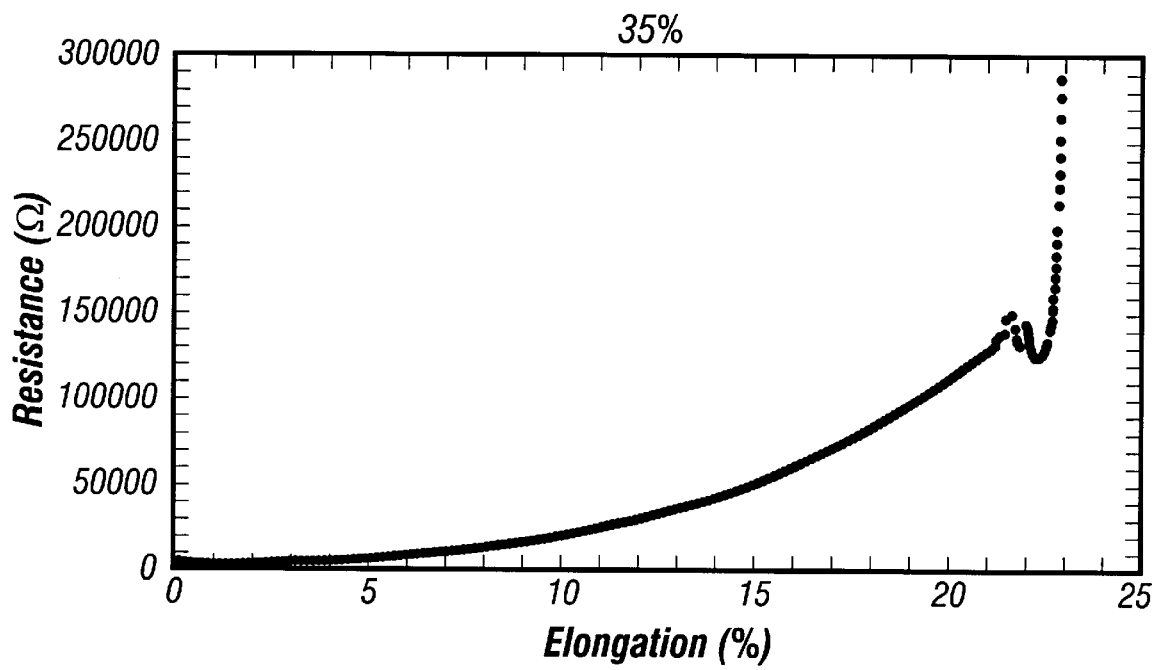
FIG. 6 is a graph indicating the relation between electric resistance of graphite-EVA (PE80 wt %) sensor and elongation (graphite concentration: 35.0 wt %)
Figure 7:
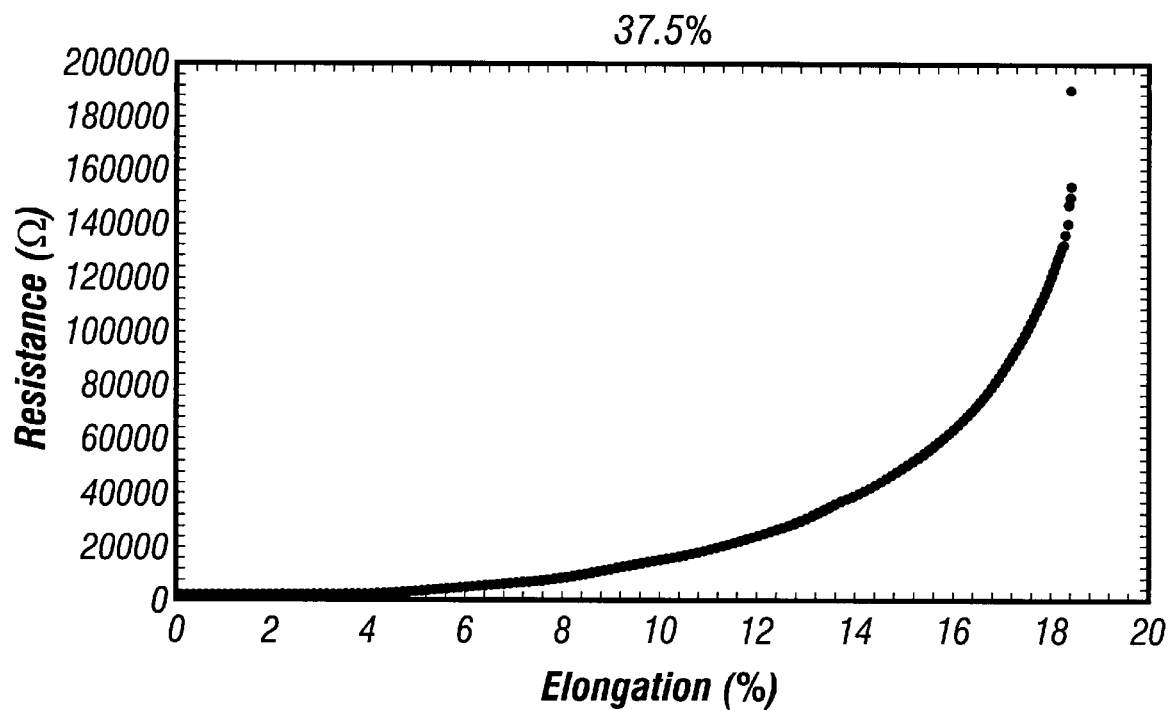
FIG. 7 is a graph indicating the relation between electric resistance of graphite-EVA (PE80 wt %) sensor and elongation (graphite concentration: 37.5 wt %)
Figure 8:
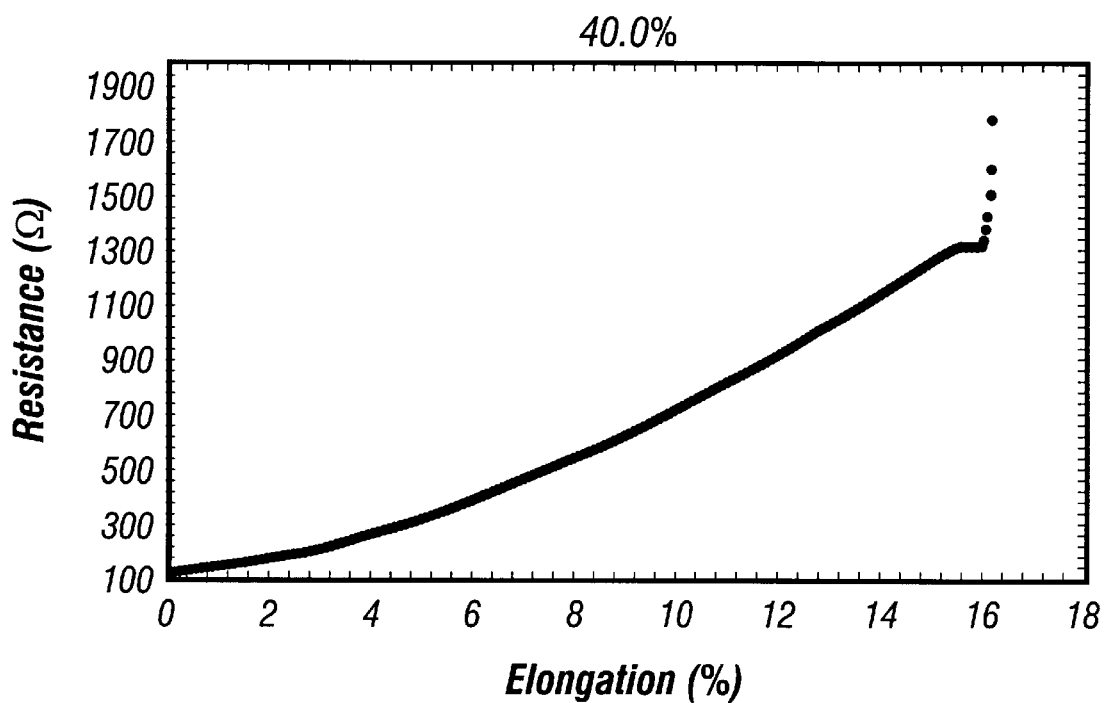
FIG. 8 is a graph indicating the relation between electric resistance of graphite-EVA (PE80 wt %) sensor and elongation (graphite concentration: 40.0 wt %)
Figure 9:
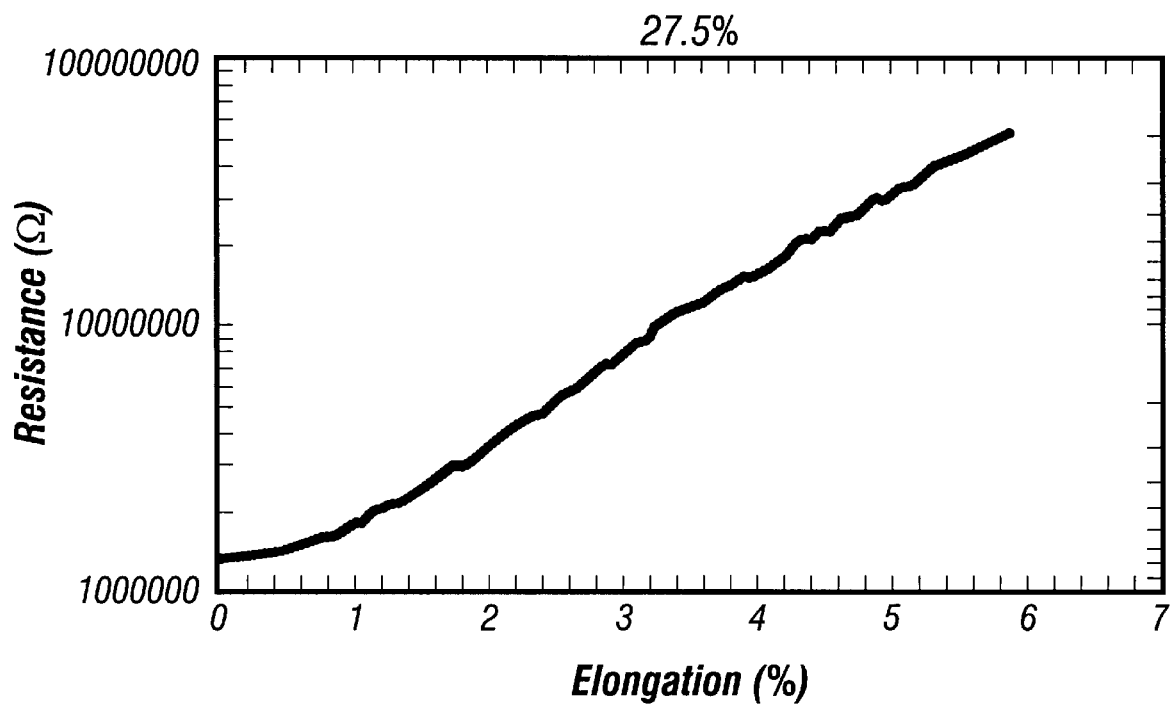
FIG. 9 is a graph indicating the relation between logarithm of electric resistance of graphite-EVA (PE80 wt %) sensor and elongation (graphite concentration: 27.5 wt %)
Figure 10:
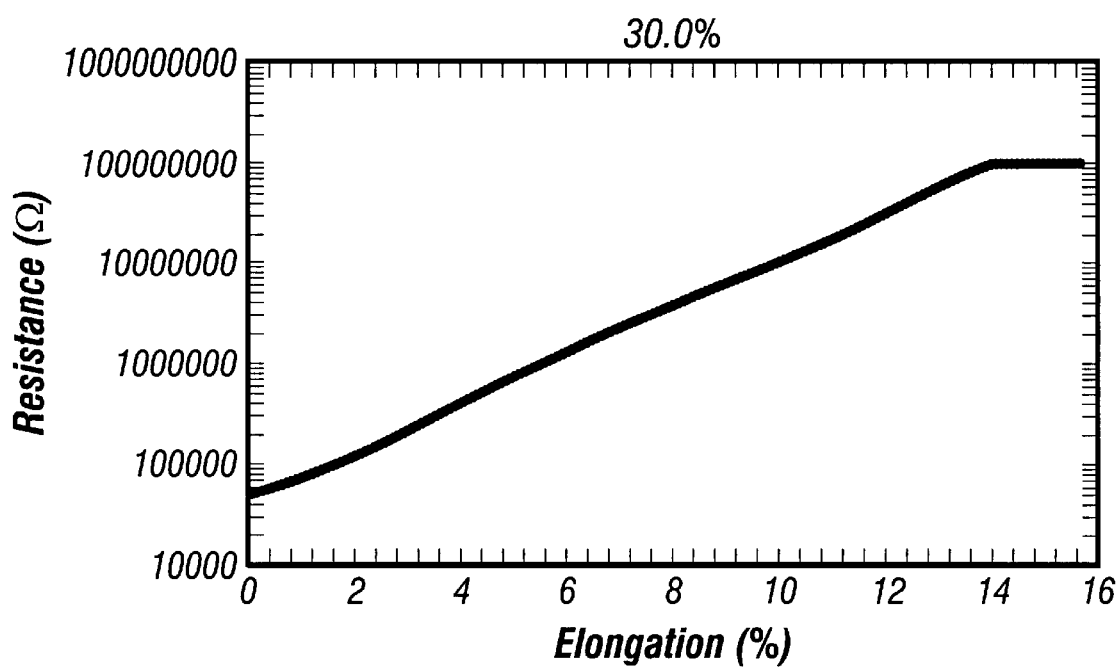
FIG. 10 is a graph indicating the relation between logarithm of electric resistance of graphite-EVA (PE80 wt %) sensor and elongation (graphite concentration: 30.0 wt %)
Figure 11:
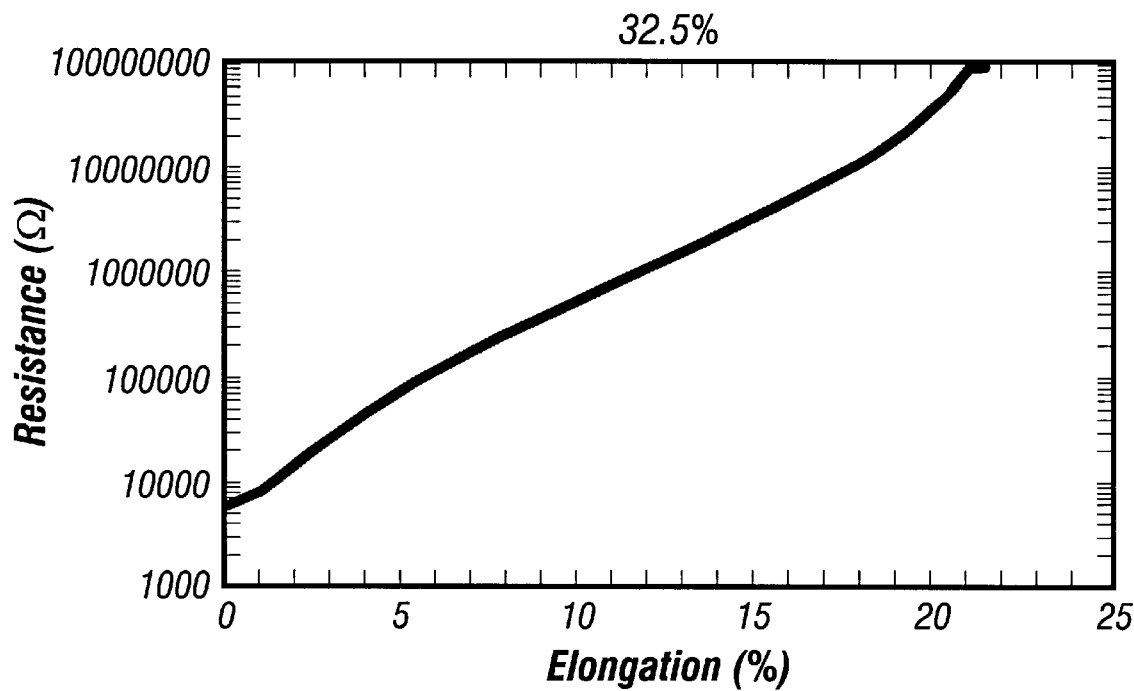
FIG. 11 is a graph indicating the relation between logarithm of electric resistance of graphite-EVA (PE80 wt %) sensor and elongation (graphite concentration: 32.5 wt %)
Figure 12:
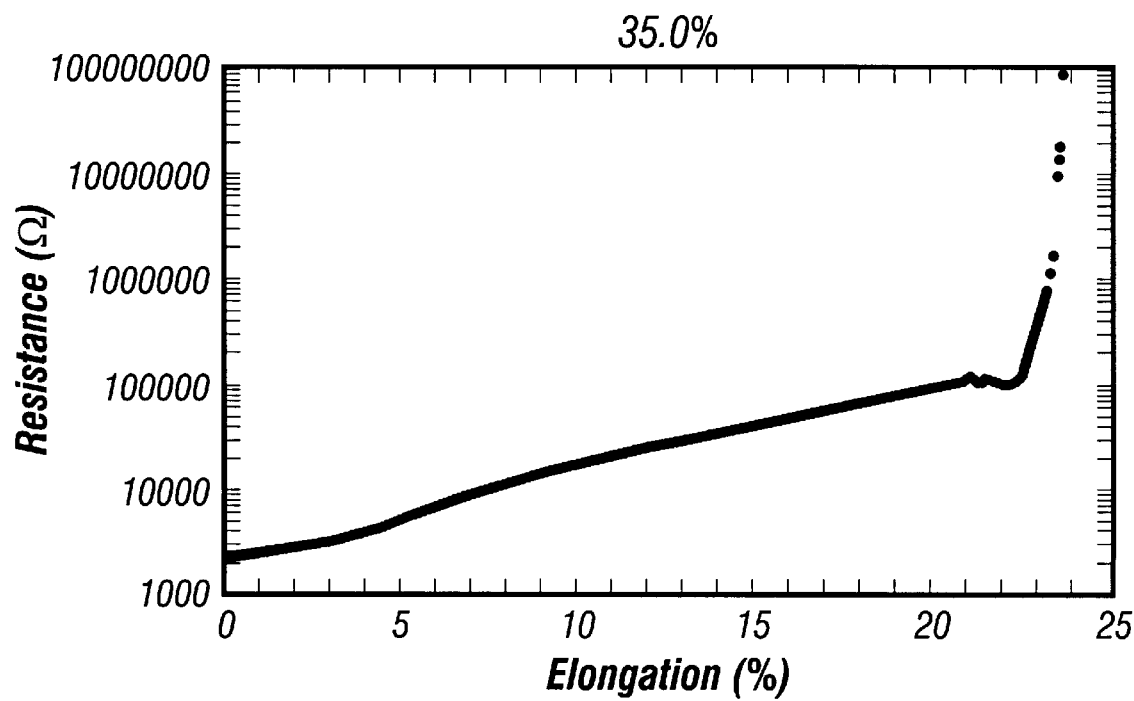
FIG. 12 is a graph indicating the relation between logarithm of electric resistance of graphite-EVA (PE80 wt %) sensor and elongation (graphite concentration: 35.0 wt %)
Figure 13:
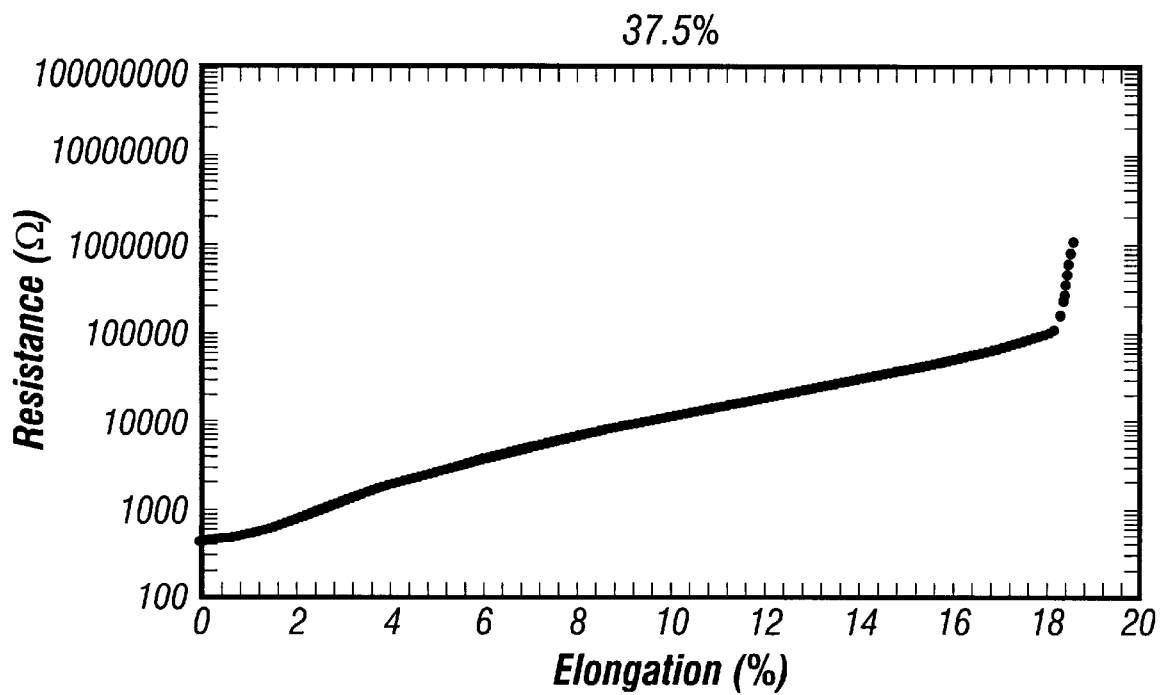
FIG. 13 is a graph indicating the relation between logarithm of electric resistance of graphite-EVA (PE80 wt %) sensor and elongation (graphite concentration: 37.5 wt %)
Figure 14:
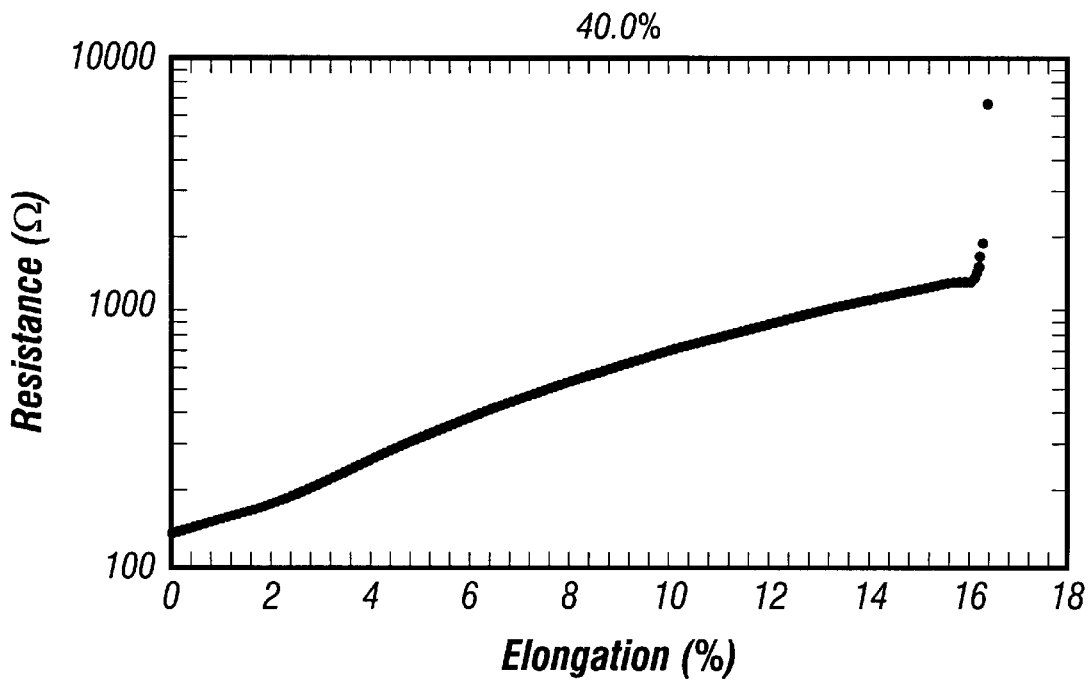
FIG. 14 is a graph indicating the relation between logarithm of electric resistance of graphite-EVA (PE80 wt %) sensor and elongation (graphite concentration: 40.0 wt %)

The relation between the resistance with no strain and the amount of graphite of the sample is shown in FIG. 2. It is seen in FIG. 2 that the resistance with no strain varies from 133Ω to 1.15 MΩ. It must be stated that an upper limit to readout the measured resistance was 100 MΩ. Resistances higher than 100 MΩ cannot be inputted into the computer.

The relation between the resistance and elongation of samples with various graphite concentrations are shown in FIGS. 3–8. The values of elongation are expressed here as ratios (%) of the elongated length to that of the original length of the central part of the dumbbell sample (25 mm). The ordinates in FIGS. 3–8 are a linear scale. It should be noted that dimensions of the scale are different. In the case of 30 wt % graphite, an exponential increase in the resistance is observable. The most remarkable increase in the resistance is observed for the 32.5 wt % graphite sample. In the case of 35.0 wt % graphite, the increase in the resistance is not so remarkable as that of 32.5 wt % graphite. The disturbance of the signal is seen in the final stage, which results in a crack of the sample. This is because the sample get brittle as the graphite concentration increases. In the case of 37.5 wt % graphite, the rate of the increase in resistance decreases, and the sample breaks at the final stage. This tendency is more remarkable in 40 wt % graphite sample.

Although the ordinates in FIGS. 3–8 are linear, resistances are plotted in the scale of logarithm as a function of elongation in FIGS. 9–14. It should be noted that a linearity is seen between the logarithm of the resistance and the elongation at each concentration of graphite. Namely the following relation holds between the resistance (R) and elongation (e).

$$\log(R) = a \cdot \epsilon + b \quad (1)$$

where a and b are constants. From (1), the following relation is derived, $$\log(R) = \log 10^{(a \cdot \epsilon)} + \log 10^b \quad (2)$$

$$R = 10^b \cdot 10^{(a \cdot \epsilon)}$$

$$R = a' 10^{b' \epsilon}$$

Then, it is clearly shown that resistance increases exponentially.

Such a linear relation between the logarithm of resistance and strain has never been reported in any journal. This relation can now be explained by tunnel current. It is expected that elongation of the sensor causes a creation of gaps between conductive particles which are joined together before elongation and enlarge gap-distances which existed already. When the gap-distances are long, no electric conduction is possible through these gaps. However, electric conduction is possible when gap-distances are short enough. This phenomenon is seen in the quantum world. For example, tennis balls cannot pass through walls but electrons can be transmitted through potential barriers. This phenomenon is called tunnel effect. The tunnel current, which is a flow of electrons by the tunnel effect, is described below.

Figure 15:
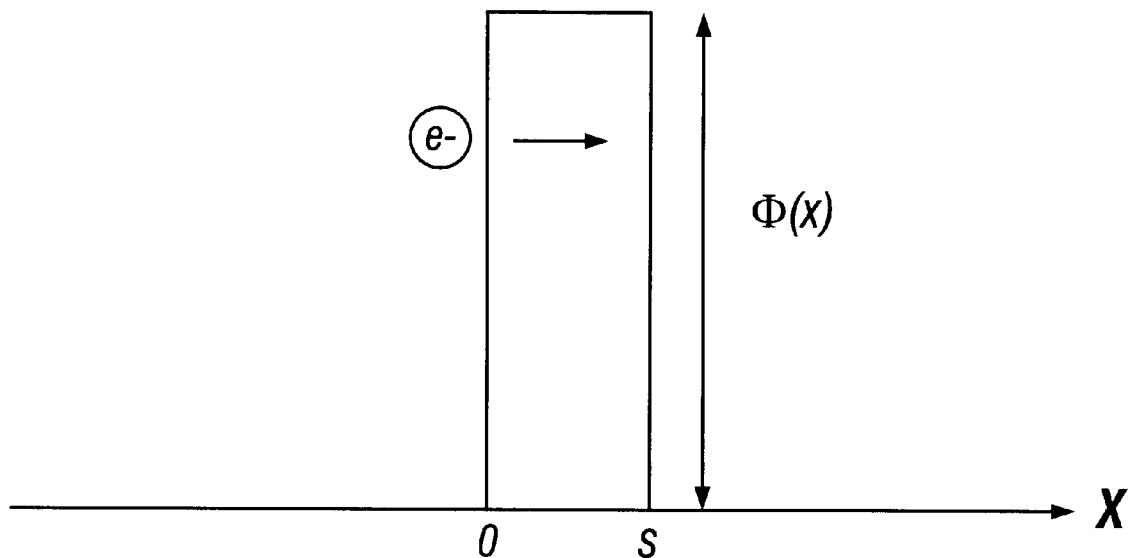
FIG. 15 illustrates a tunnel junction wherein electrons pass quantum-mechanically through the potential barrier of which the height and width are $\phi(x)$ and s.

Let the probability for an electron traveling in the X-direction with a kinetic energy (Ex) passing through a potential barrier as shown in FIG. 15 whose thickness and height are s and f(x), respectively, be P(Ex). Then this probability is expressed as, $$P(E_x) = \exp\{(-4\pi/h)\int_0^s [2m(\phi(x)-E_x)]^{1/2} dx\} \quad (3)$$

where m, h, s and $\phi(x)$ are the mass of an electron, Plank's constant, the width of the potential barrier, and the height of the potential barrier, respectively. Using this probability, the tunnel current density can be expressed as follows.

$$J = \int_0^{Em} P(E_x) dE_x \{(4\pi m e/h^3) X \int_0^\infty [f(E)-f(E+eV)] dE_r\} \quad (4)$$

where f(E) is a Fermi-Dirac distribution function and Er is the kinetic energy to radial direction perpendicular to X axis. Since Equation (4) cannot be integrated mathematically, some approximation is necessary. Here the approximation by Simmons (J. G. Simmons, J. Appl. Phys., 34, 1793 (1963)) is employed. When the voltage across the potential barrier is low, the tunnel current is expressed as, $$J=[3(2m\phi)^{1/2}/2s](e/h)^2 V \cdot \exp[-(4\pi s/h)(2m\phi)^{1/2}] \quad (5)$$

Since electric field (F) across the potential is given by F=V/s, the following relation is given between the conductance(s) and the width of the barrier(s).

$$\log(\rho)=\log[3(2m\phi)^{1/2}/2](e/h)^2-[(4\pi s/h)(2m\phi)^{1/2}] \quad (6)$$

Since the conductance s is the reciprocal of the volume resistance, then the volume resistance r is given as, $$\log(\rho)=[(4\pi/h)(2m\phi)^{1/2}](s)-\log[3(2m\phi)^{1/2}/2](e/h)^2 \quad (7)$$

Namely, the relation between the logarithm of the resistance and the width of the tunnel barrier is linear.

The experimental results in FIGS. 9–14 are not explicable directly from Equation (7). This is because Equation (7) is derived from the single tunnel junction. Actually there are numerous of tunnel junctions (tunnel barriers) in a sample. This point must be taken into account. The inventors have made a simulation with various calculation model and found that the linearity between the logarithm of resistance and elongation always hold whatever model is used. Therefore, the inventors conclude that the linearity between logarithm of resistance and elongation is explicable in terms of the tunnel effect. The details should be referred to the reference (T. Kimura, N. Yoshimura, T. Ogiso, K. Maruyama and M. Ikeda, Polym. Commun.).

Figure 16:
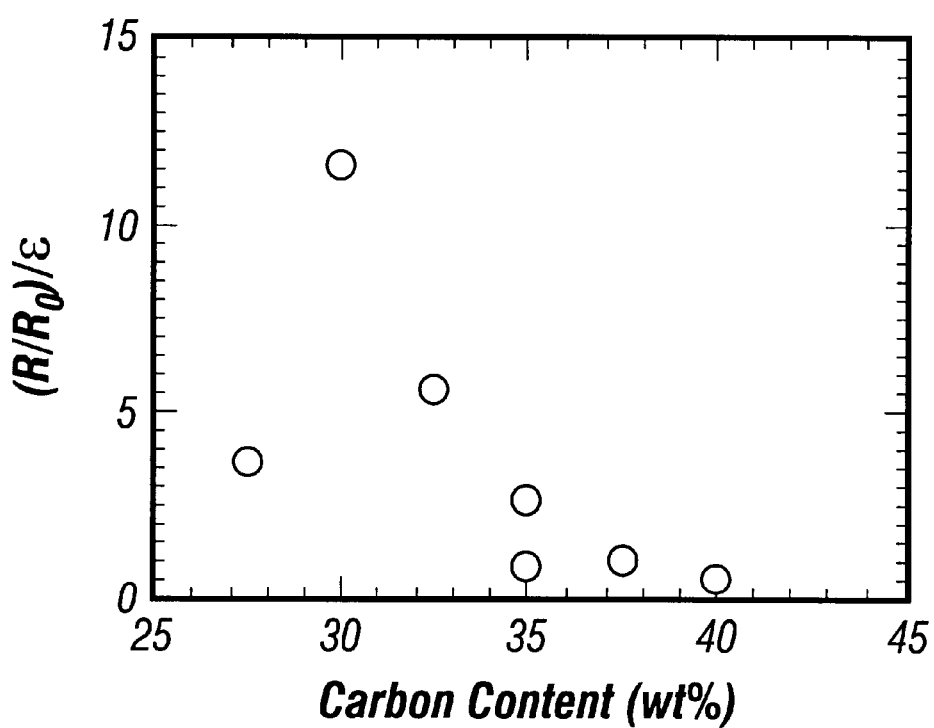
FIG. 16 is a graph indicating the relation between the increased ratio of electric resistance per unit elongation and graphite concentration.

The theoretical explanation is given for the linearity between the logarithm of resistance and elongation. Then, the effect of graphite concentration on the linearity should be referred. Let the resistance of a sensor which is not elongated, namely with no stress, be Ro. Let the resistance of the sensor elongated by e be R. Then, a comparison can be made by taking the value of [(R/Ro)/e]. Namely this value indicates the multiple number of resistance per unit elongation. This is shown in FIG. 16. As seen in FIG. 16, the value of [(R/Ro)/e] is the highest when the graphite concentration is 30 wt %. Thus, the most sensitive sensor is obtained around this carbon concentration. The relation between carbon concentration and [(R/Ro)/e] could be explained as follows. Namely, when carbon concentration is low, potential barriers are high because gap distances are longer. The tunnel current is extremely low in this case and actually unable to be measured. Thus, the increase in the resistance is not expected too much for those sensors of lower carbon concentration. On the other hand, in the case of high carbon concentration, a higher increase in resistance cannot be expected because carbon particles contact each other directly and tunnel conduction could be minor. Thus, the inventors can expect that the maximum value appear at certain carbon concentration as seen in FIG. 16.

Embodiment 2

In the EMBODIMENT 1, the effects of graphite concentration in graphite-EVA composites are described precisely. Several embodiments are described hereafter where various conductive particles are used.

EVA (9.4 g) was dissolved in toluene (90 g), and Ketjenblack (0.6 g), which was crushed in a moter with a pestol in advance, was dispersed. The solution of EVA-Ketjenblack-toluene was casted in a small rectangular pan with a teflon coat, and toluene was evaporated. Samples were made from this composite by hot-press, and electrodes were given with silver paint as described in EMBODIMENT 1 (see also FIG. 1).

Figure 17:
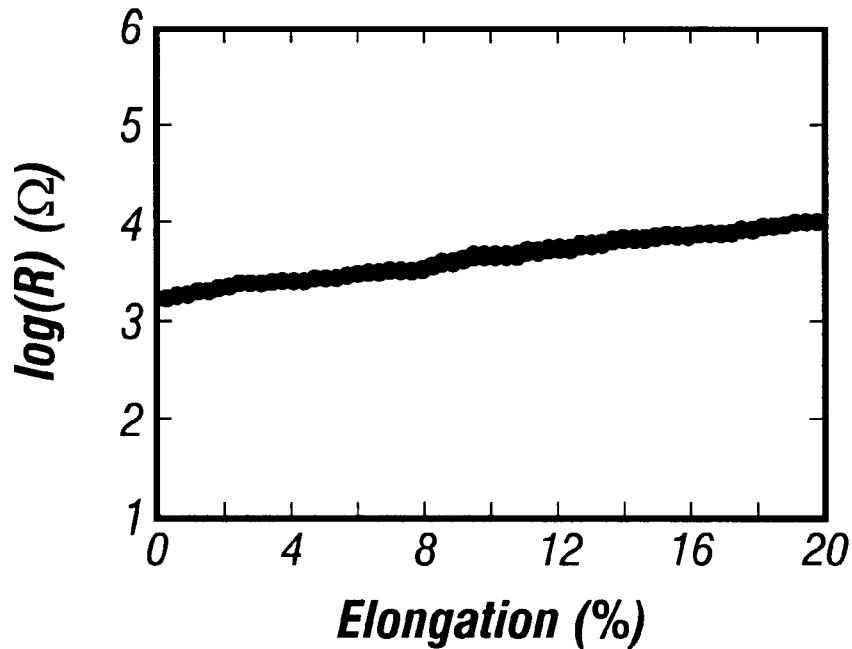
FIG. 17 is a graph indicating the relation between elongation of 6 wt % Ketjenblack-EVA (ethylene 75%) system and electric resistance.

Resistances and elongations of 6 wt % Ketjenblack-EVA samples were measured by the same procedure as described in EMBODIMENT 1. The result is shown in FIG. 17. As seen in FIG. 17, the increase in resistance is lower than that in EMBODIMENT 1. With the increase in elongation, the resistance does not increase as in the case of other composites. The increase of resistance as a result of elongation is the lowest in the case of Ketjenblack, as will be described later. Although the reason for this is now being studied, it can be said that this is caused by a strong interaction between the particles of Ketjenblack.

Embodiment 3

Figure 18:
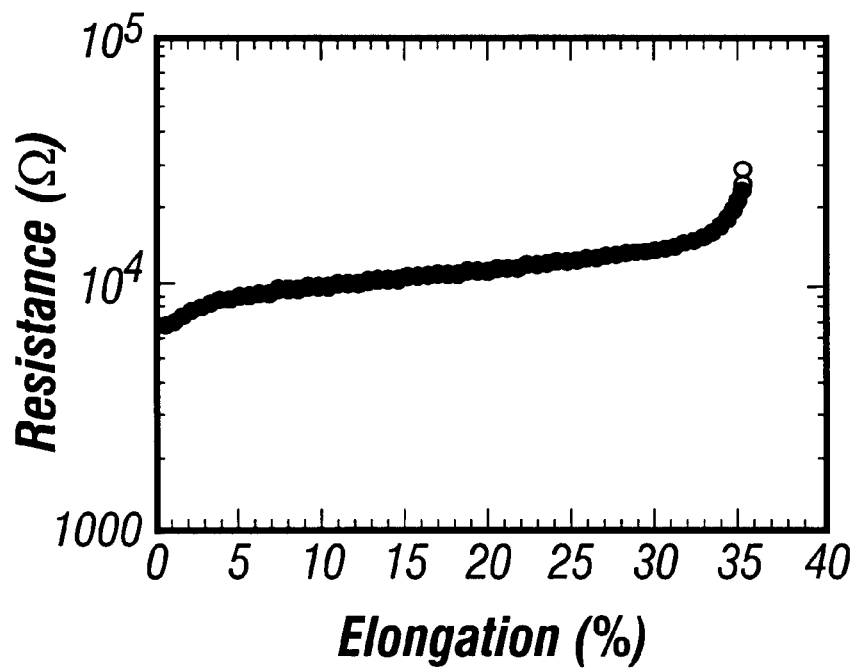
FIG. 18 is a graph indicating the relation between elongation of 6 wt % acetylene black-EVA (ethylene 75%) system and electric resistance.

In this case, acetylene black was employed. In 90 g of toluene, 10 g of EVA (ethylene: 75 wt %, vinyl acetate: 25 wt %) was dissolved. In this solution, 2.5 g of acetylene black was dispersed. The solution of EVA-acetylene black-toluene was casted in a small rectangular pan with a teflon coat, and toluene was evaporated. Samples were made from this composite by hot press, and electrodes were given with silver paint as described in EMBODIMENT 1. The relation between the resistance and the elongation is shown in FIG. 18. The result in FIG. 18 is similar to that in FIG. 17. Though elongation increases, the resistance does not increase too much as in the case of Ketjenblack. However, an increment of resistance can be higher when the concentration of acetylene black is lowered to the percolation threshold.

Embodiment 4

Figure 19:
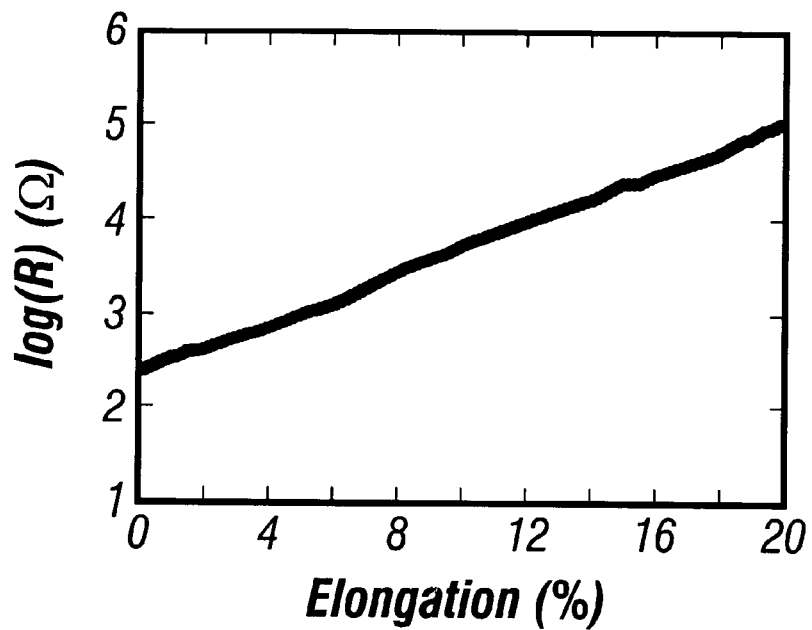
FIG. 19 is a graph indicating the relation between elongation of 6 wt % acetylene black-EVA (ethylene 75%) system and electric resistance.

Potassium titanate is an insulator and forms needle type crystals. This is used for reinforcement of micro-sized plastics such as the gears of wrist watch. This is useful as micro-fillers. These micro-fillers change to be conductive by a carbon coating on their surfaces. This is done by CVD (chemical vapor deposition). In 90 g of toluene, 10 g of EVA (ethylene: 80 wt %, vinyl acetate: 20 wt %) was dissolved. In this solution, 5.385 g of carbon coated potassium titanate (Ohtsuka Chemicals Dentall WK-200B) was dispersed. The solution of EVA-[WK-200B]-toluene was casted in a small rectangular pan with a teflon coat, and toluene was evaporated. Samples were made from this composite by hot press, and electrodes were given with silver paint as described in EMBODIMENT 1. The relation between the resistance and the elongation is shown in FIG. 19. In this case, a considerable increase in the resistance with an increase of elongation is clearly seen. This is different from the results of fine carbons in FIGS. 17 and 18.

Embodiment 5

Figure 20:
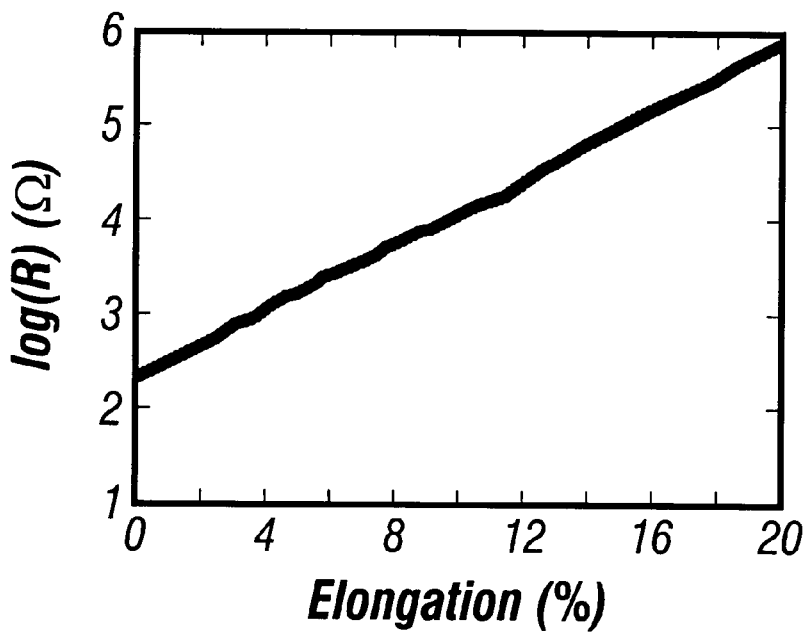
FIG. 20 is a graph indicating the relation between elongation of 30 wt % Ni-coated mica-EVA (ethylene 80%) system and electric resistance.

70 weight parts of EVA (vinyl acetate: 20 wt %, ethylene: 20 wt %) was dissolved in toluene. Into this solution, 30 weight parts of mica particles coated with nickel by a chemical plating were dispersed. Dumbbell-shape samples were made, and the relation between resistance and elongation was obtained by the same procedure described above. The results are shown in FIG. 20, and a similar high increase in the resistance is seen as in the case of the EMBODIMENT 4.

Embodiment 6

Figure 21:
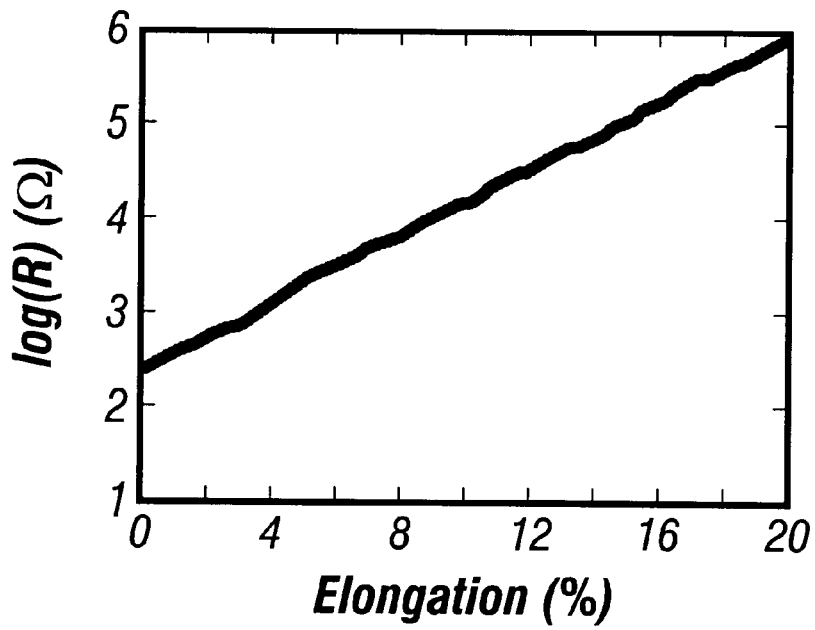
FIG. 21 is a graph indicating the relation between elongation of 35 wt % graphite (J-SP)-hard polyvinyl chloride system and electric resistance.

Hereafter, the embodiments use various polymers. As polyvinylchloride, a sheet of polyvinylchloride (soft type) was used. After cutting into small pieces, polyvinylchloride of 65 wt % was heated to a molten state. Graphite (Nihon Kokuen J-SP) of 35 wt % was dispersed and pressed into a dumbbell shape. By giving the electrode with silver paint, the measurements were done as described above. The result is shown in FIG. 21. In this case, the increase in the resistance with an increase of elongation is clearly noticed.

Embodiment 7

Figure 22:
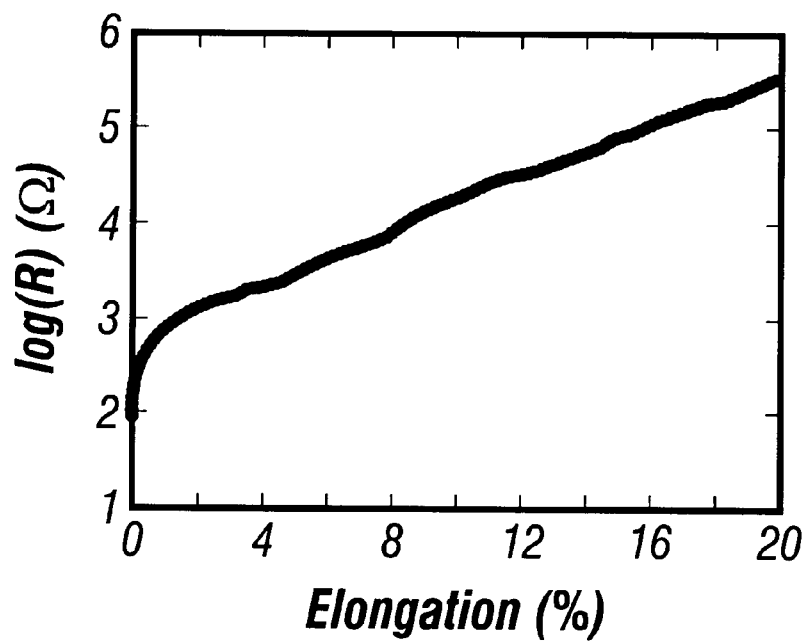
FIG. 22 is a graph indicating the relation between the elongation of 35 wt % graphite (J-SP)-soft polyvinyl chloride system and electric resistance.

As a polymer of the strain sensor, silicone is used in this embodiment. Silicone elastomer (Toray Dow Corning SE9187) of 65 wt % was mixed with toluene (30 wt %), and then graphite (Nihon Kokuen, J-SP) 35 wt % was dispersed therein. This mixture was molded in a dumbbell shape which is the same as that in FIG. 1. After allowing toluene to be evaporate, this was dried in vauo. Electrodes were given with the same procedure described above. There was somewhat a problem on the adhesion of silver paint. Therefore, it would be better to use wire-mesh electrodes instead of silver paint in the case of manufacture. The measurements were carried out, and the result is shown in FIG. 22. When silicone elastomer is hardened, there could be strain inside the sample. The first part of the curve in FIG. 22 at lower elongation may be due to this strain remaining in the sample. However, the resistance increases sharply when the linear plot is made. This implies that this graphite-silicone composite can be used as a strain sensor.

Embodiment 8

Figure 23:
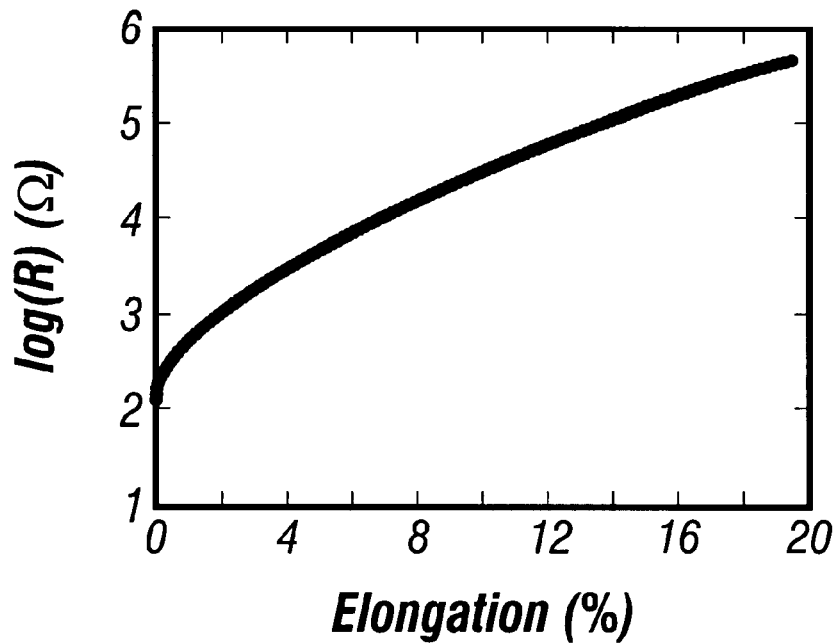
FIG. 23 is a graph indicating the relation between the elongation of 35 wt % graphite (J-SP)-acrylonitrile-butadiene rubber system and electric resistance.

In this embodiment, a rubber is used as a polymer of the sensor. In 50 ml of toluene 6.5 g, acrylonitrile-butadiene rubber, which was not vulcanized, was dissolved, and 3.5 g of graphite (Nihon Kokuen, J-SP) was dispersed. The preparation and measurement of samples were done by the same procedure as that of EMBODIMENT 7. The result is shown in FIG. 23. As in the case of EMBODIMENT 7, the first part of the curve in FIG. 23 deviates slightly from a straight line. However, this composite can be used as a strain sensor.

Embodiment 9

Figure 24:
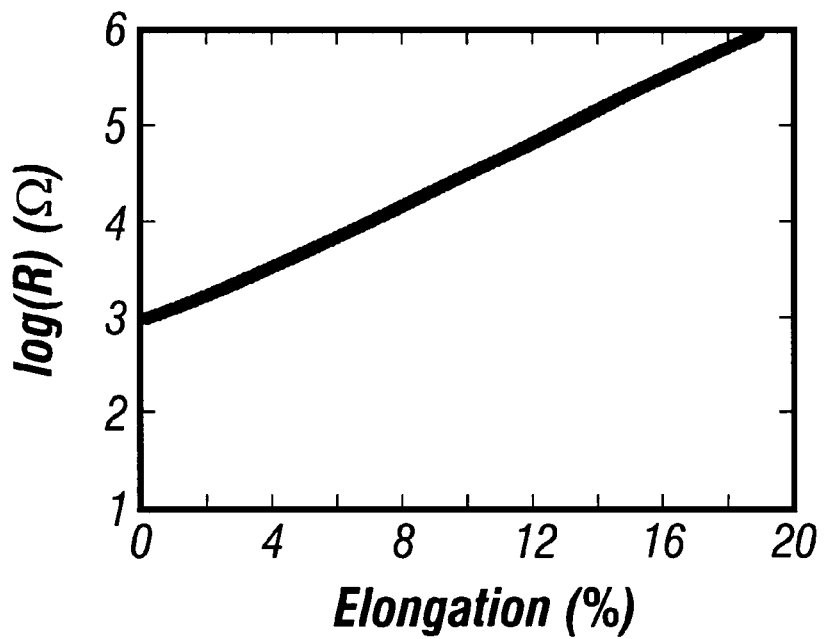
FIG. 24 is a graph indicating the relation between the elongation of 35 wt % graphite (J-SP)-low density polyethylene (petro) and electric resistance.

As in the case of EMBODIMENT 6, polymer is used in a molten state. Low density polyethylene (Toso, Petrocene) of 65 g, and graphite (J-SP) of 35 g were mixed in a kneader, and samples were made by hot press. Measurement of resistance and elongation were made by the same process as described above. The result is shown in FIG. 24. It should be noted that an excellent linearity holds between the logarithm of resistance and elongation.

Embodiment 10

Figure 25:
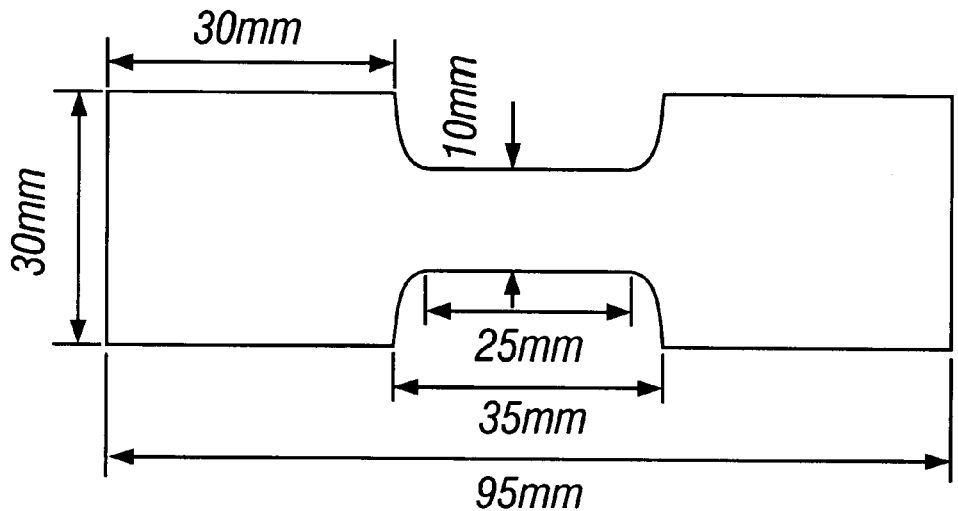
FIG. 25 is a top view showing the shape of a sample sensor wherein the sensor is painted with a conductive silver paste at both ends thereof.
Figure 26:
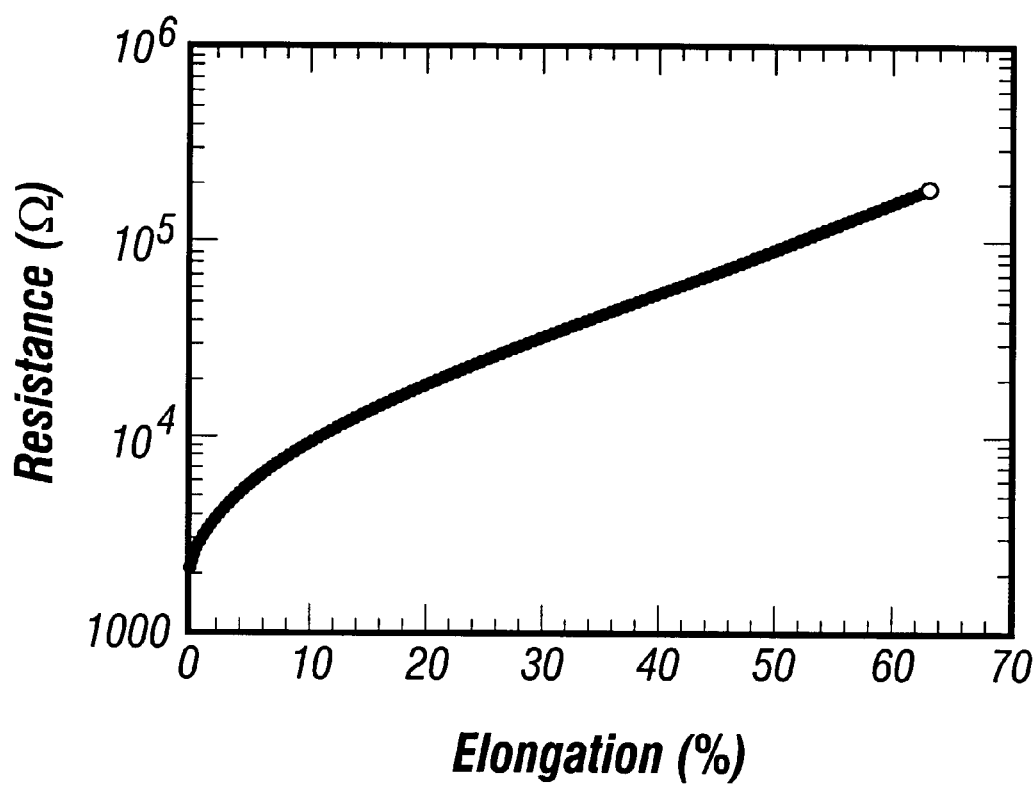
FIG. 26 is a graph indicating the relation between the elongation of 35 wt % graphite (CSP)-EVA system of PET print sample and electric resistance.

Hereafter, the embodiments by the printing process are described. Using tetraline as a solvent, an ink [35 wt % graphite (Nihon Kokuen, CSP)-EVA (ethylene 20 wt %)] was made. Strain sensors were printed with this ink by screen printing. The base film was PET (0.12 mm in thickness) which was processed with two axes elongation. Electrodes were printed on the PET before printing with the ink. Samples were dried in an IR furnace. The thickness of the print layer (which does not include the thickness of the base film) was 0.09 mm. The design of the sample is shown in FIG. 25. The measurement of the resistance and elongation were done by the same procedure. The result is shown in FIG. 26. As seen in FIG. 26, though some deviation is recognizable at first, the linearity holds between the logarithm of resistance and elongation. When resistances are plotted in a linear scale, it is found that resistance increases abruptly from a certain amount of elongation. Thus, it is confirmed that this can be used as a strain sensor.

Embodiment 11

Figure 27:
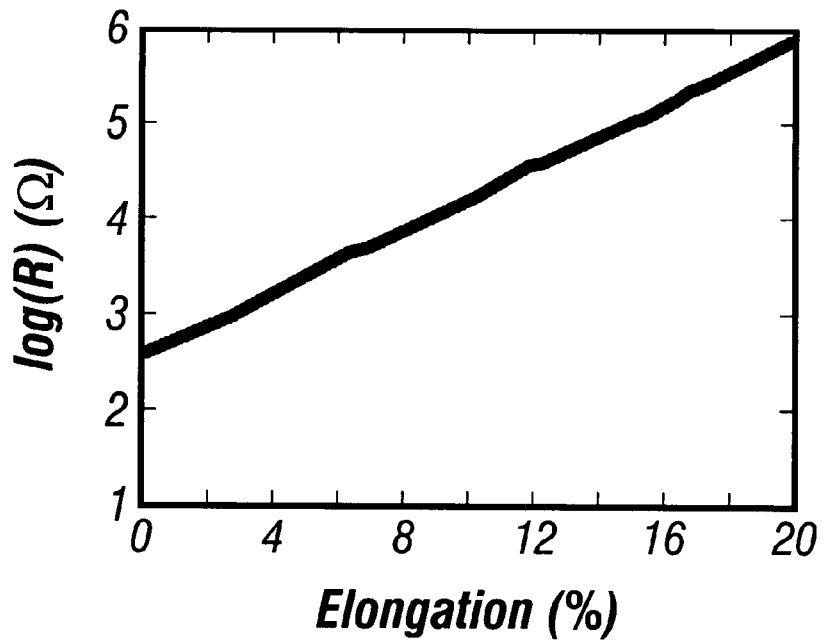
FIG. 27 is a graph indicating the relation between the elongation of a sample on which a 35 wt % graphite (CSP)-EVA system is printed in polycarbonate film and electric resistance.

Ink was made with 35 wt % of graphite (Nihon Kokuen, CSP) 65 wt % of EVA (ethylene 20 wt %). The solvent was tetraline. Samples were printed on polycarbonate film with this ink and dried by the same procedure as described above. The thickness of the printed layer and the base film were 0.1 mm. The measurements were carried out, and the result is shown in FIG. 27. The good linearity holds between the logarithm of resistance and elongation. Thus, this can be used as strain sensors.

Embodiment 12

Figure 28:
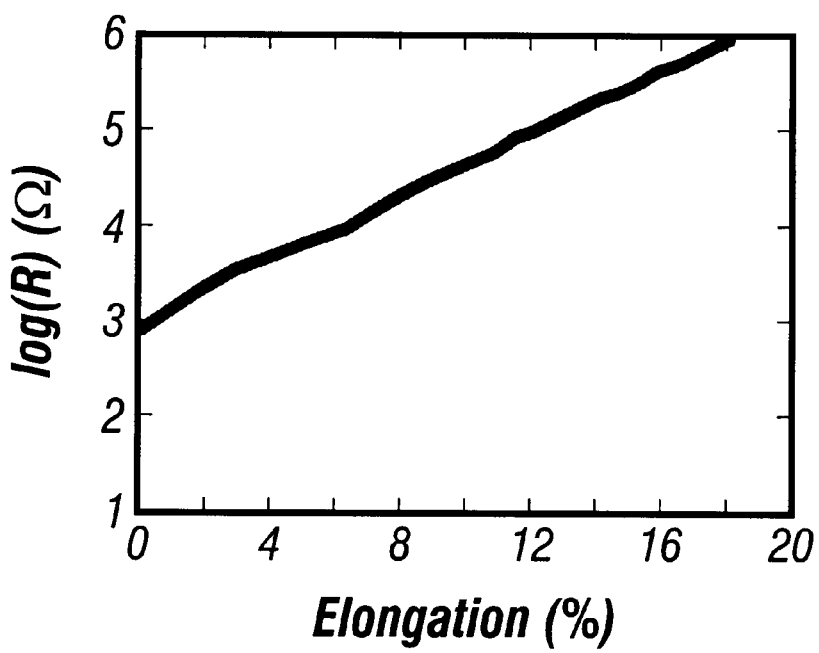
FIG. 28 is a graph indicating the relation between the elongation of a sample on which a 35 wt % graphite (CSP)-EVA system is printed in hard polyvinyl chloride film and electric resistance.

Sensors were printed on polyvinyl chloride films (hard type 0.1 mm in thickness) with the ink (35 wt % graphite (CSP)-EVA (ethylene 20 wt %)). Sample preparation and measurements were done by the same procedure as described above. The result is shown in FIG. 28. As seen from FIG. 28, similar results are obtained as in previous EMBODIMENTS. Thus, this can also be used as strain sensors.

Embodiment 13

Figure 29:
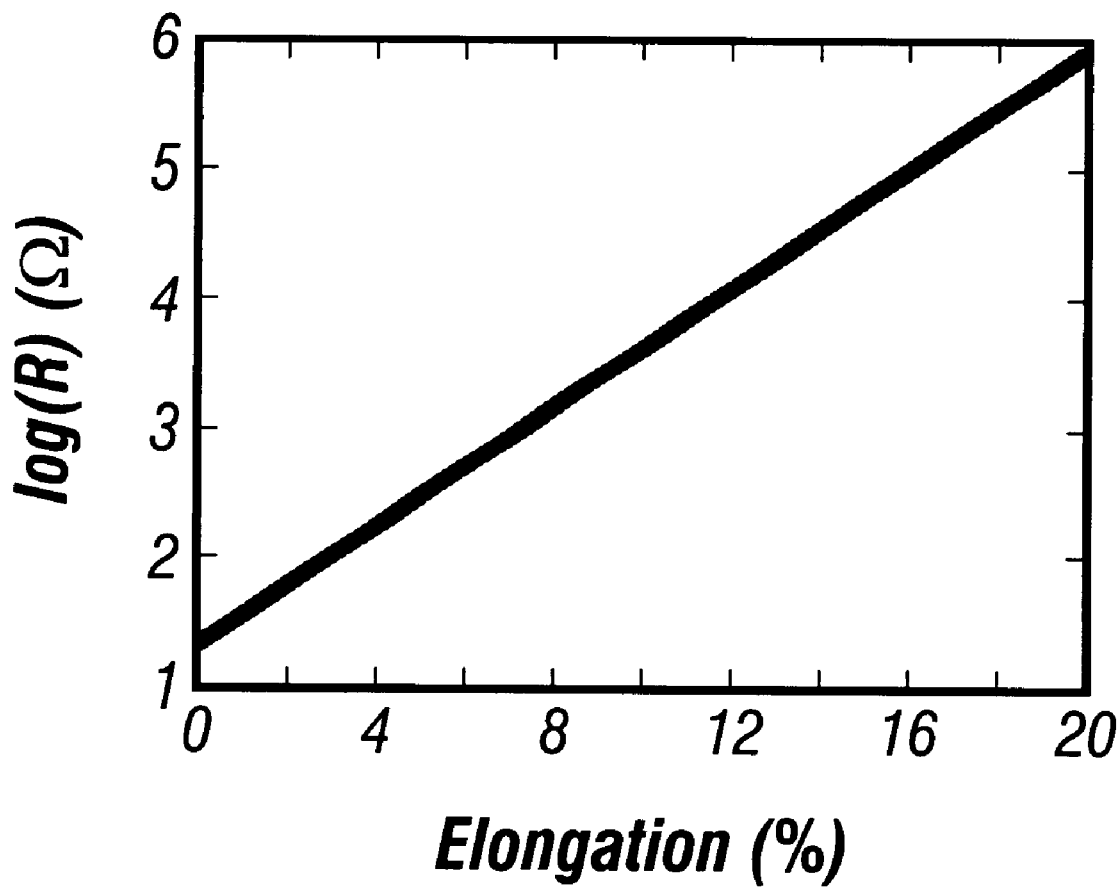
FIG. 29 is a graph indicating the relation between the elongation of a sample on which a 35 wt % graphite (CSP)-EVA system is printed in polyimide film and electric resistance.

65 wt % of EVA (ethylene 80 wt %) was dissolved in tetraline, and 35 wt % of graphite (Nihon Kokuen, CSP) was added so as to make ink. Samples were made by printing this ink on polyimide films (Ube Upilex 125 μm). The shape of the samples was the same as that in EMBODIMENT 10. The relation between resistance and elongation was obtained. The result is shown in FIG. 29. As seen from FIG. 29, a good result is obtained in this case as well.

As described above, it was found that the elongation of polymer systems dispersed with carbon causes an exponential increase in their resistance. It was also found from the above EMBODIMENTS that the highest increase in the resistance appeared at a carbon concentration around 30 wt %. From the data shown above, it is possible to design sensors which show a sharp increase in the resistance at a strain which is allowable for the safety. It is quite easy to make a standard of safety monitoring if sensors with exponential output are employed. However it would be very difficult and need a lot of effort to settle a critical value for safety if the outputs of sensors are linear. In addition, the reliability of that critical value might be suspicious. As to the change of resistance over a long time, even sensors of which variation of resistance is several tens % after a long period can be used without any problem if the change in the resistance is higher than two orders of magnitude at a monitored strain. From this point, the sensors of the present invention have excellent characteristics which have never seen before.

It is shown in the above EMBODIMENTS that the high value of $[(R/R_o)/e]$ is advantageous to design sensors. Except for higher values of $[(R/R_o)/e]$, it is also advantageous to make use of mechanical properties of the sensors. For sensors with a higher carbon content, the sharpness of the variation in resistance is sacrificed, but sensors turn to be fragile. This makes the sensors to be cut when they have strain. In this case, the fact that the sensors had strain can be recorded as a fact that the sensors are cut. On the other hand, for sensors with a lower carbon content, the elongated sensors can be recovered to their original state when stress is removed. In order to use sensors for 24 hours, continuous monitoring of sensors with lower carbon content can be useful.

A wide selection of the resistance is obtainable by barring carbon content. By barring the distance between electrodes, it is also possible to have a clear increase in the resistance of the sensors, which are installed and strained at a critical region. With such selections (in carbon content and electrode distance), large-sized sensors are available; and only with those sensors, it becomes possible to monitor buildings, ships, mega-float and so on.

There are two important factors in monitoring the variations of resistance in polymer-carbon systems which are elongated. One is carbon itself. Though the result would be different depending on the type of carbon, it is conceivable that the variation of resistance with strain is less when Ketjenblack, which has strong interaction, is used. On the other hand, in the case of graphite, a large variation of resistance can be expected. Therefore, sensors suitable for desired purposes can be made by selecting the type of carbon.

As for the polymers, it is obvious from the above EMBODIMENTS that basically any type of polymer can be used for the sensors as long as they can be elongated in the desired elongation range. For a future development of the sensors, two factors, elasticity and viscosity, must be taken into a consideration independently. Viscosity is predominant in a polymer such as isoprene. In these polymer systems, strained resistance tends to remain even if the stress is removed. On the other hand, in polymer systems where an elastic nature dominates, resistance tends to recover the original value when the stress is removed. Therefore, by checking their visco-elastic nature, it is possible to select polymers for continuous monitoring systems or spot monitoring systems.

We claim:

1. Strain sensors wherein said strain sensor is formed in a sheet shape from composites, and said sheet shape strain sensor is fixed to an exterior of iron and iron-concrete structural products, said composites consisting of polymers and individual conductive particles dispersed in said polymers, and a strain of said composites causes changes in a distance between said conductive particles and a corresponding change in electric resistance of said composites so as to recognize values of said strain.

2. Strain sensors as set forth in claim 1, wherein said composites are formed by dispersing said conductive particles into a polymer solution or polymer solutions where more than two kinds of polymers are dissolved and by evaporating a solvent, thus molding into a sheet shape.

3. Strain sensors as set forth in claim 1, wherein an ink is made by dispersing conductive particles into a polymer solution or polymer solutions where more than two kinds of polymers are dissolved, and the sensors are made by dipping a base into the ink or printing the ink on a base followed by a drying process.

4. Strain sensors as set forth in claim 1, wherein sensors are made with thermoplastic dispersed with conductive particles and molded into a sheet shape.

5. Strain sensors as set forth in claim 1, wherein sensors are made by thermocured plastics and their hardening agents dispersed with conductive particles and then cured into a sheet shape.

6. Strain sensors as set forth in claim 1, wherein said conductive particles are carbon black, graphite, activated carbon, carbon whiskers, fullerenes, carbon nanotubes, metallic powder, metallic foils, beads and microbeads of insulators whose surfaces are turned to be conductive with carbon, or micro pieces of insulators including mica and potassium titanate whose surfaces are changed to be conductive by chemical plating, CVD (chemical vapor deposition) or PVD (physical vapor deposition).

7. Strain sensors as set forth in claim 1, wherein said polymer is polyethylene, polypropylene, polyacrylate, polyesters, nylons, polyvinyl chloride, polyvinylidene chloride, fluoropolymers, polyvinyl acetate, polystyrene, polymethylmethacrylate, polyethylmethacrylate, polyhydroxymethyl methacrylate, polyvinyl alcohol, polyacrylonitrile, polyimide, polysulfone, polycarbonate, polyacetal, polyurethane, polyphenylene oxide, polyxylene, polyformal, polybutylal, polyoxyethylene, polyoxymethylene (amorphous), copolymers of two or more monomers of which homopolymers are described above, rubbers, silicone polymers, phenol polymers, alkid polymers or cellulose polymers.

8. Strain sensors as set forth in claim 7, wherein copolymers of two or more monomers are ethylene-vinylacetate copolymers.

9. The strain sensor according to claim 1, wherein a resistance value of the strain sensors is expressed by the formula:

$$R = a 10^{be}$$

wherein a and b are constants and e is amount of elongation of the strain sensor caused by the strain.

* * * * *